United States Patent
Reed et al.

[11] Patent Number: 5,772,893
[45] Date of Patent: Jun. 30, 1998

[54] ETHER DIPHOSPHONATE SCALE INHIBITORS

[75] Inventors: Peter E. Reed, Plainfield; Michael A. Kamrath, Aurora; Phillip W. Carter, Naperville; Ronald V. Davis, Geneva, all of Ill.

[73] Assignee: NALCO Chemical Company, Naperville, Ill.

[21] Appl. No.: 696,450

[22] Filed: Aug. 13, 1996

[51] Int. Cl.⁶ .................................................. C02F 5/14
[52] U.S. Cl. .................. 210/699; 210/700; 252/180; 252/389.2; 252/389.21; 422/14; 562/13; 562/21
[58] Field of Search ................... 210/699, 700; 252/180, 181, 389.2, 389.21, 389.22; 422/15; 562/13, 21

[56] References Cited

U.S. PATENT DOCUMENTS

| | | | |
|---|---|---|---|
| 3,617,576 | 11/1971 | Kerst | 210/699 |
| 3,957,160 | 5/1976 | Plöger et al. | 210/700 |
| 4,088,678 | 5/1978 | Matt et al. | 210/699 |
| 4,172,787 | 10/1979 | Ries et al. | 210/699 |
| 4,246,103 | 1/1981 | Block et al. | 210/699 |
| 4,892,679 | 1/1990 | Blum | 562/21 |
| 4,960,928 | 10/1990 | Klose et al. | 562/21 |
| 5,259,974 | 11/1993 | Chen et al. | 210/700 |
| 5,414,112 | 5/1995 | Dragisich | 562/12 |
| 5,478,476 | 12/1995 | Dragisich | 210/700 |
| 5,500,128 | 3/1996 | Robertson | 210/699 |

*Primary Examiner*—Peter A. Hruskoci
*Attorney, Agent, or Firm*—Thomas M. Breininger; Kelly L. Cummings

[57] ABSTRACT

The invention is a method for the prevention of scale formation on metal or other surfaces in contact with scale-forming industrial water with an effective scale-inhibiting amount of an ether 1,1-diphosphonate of the general formula:

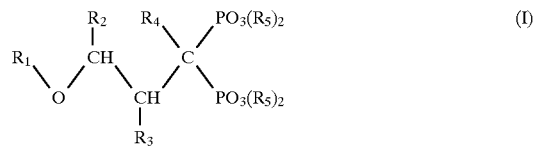

The invention is also a method for the prevention of corrosion on metal surfaces in contact with corrosive industrial water with an effective corrosion-inhibiting amount of an ether 1,1-diphosphonate of the same general formula. A preferred ether 1,1-diphosphonate is 1,1, diphosphono-4,7-dioxaoctane for both methods.

28 Claims, No Drawings

ETHER DIPHOSPHONATE SCALE INHIBITORS

FIELD OF THE INVENTION

The invention is a method for the prevention of scale formation on metal or other surfaces in contact with scale-forming industrial water with an effective scale-inhibiting amount of a 1,1 ether diphosphonate of the general formula:

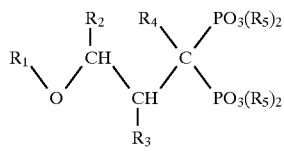

The invention is also a method for the prevention of corrosion on metal surfaces in contact with corrosive industrial water with an effective corrosion-inhibiting amount of an ether 1,1-diphosphonate of the same general formula. A preferred ether 1,1-diphosphonate is 1,1, diphosphono-4,7-dioxaoctane for both methods.

BACKGROUND OF THE INVENTION

The utilization of water which contains certain inorganic impurities, and the production and processing of crude oil water mixtures containing such impurities, is plagued by the precipitation of these impurities with subsequent scale formation. In the case of water which contains these contaminants the harmful effects of scale formation are generally confined to the reduction of the capacity or bore of receptacles and conduits employed to store and convey the contaminated water. In the case of conduits, the impedance of flow is an obvious consequence. However, a number of equally consequential problems are realized in specific utilizations of contaminated water. For example, scale formed upon the surfaces of storage vessels and conveying lines for process water may break loose and these large masses of deposit are entrained in and conveyed by the process water to damage and clog equipment through which the water is passed, e.g., tubes, valves, filters and screens. In addition, these crystalline deposits may appear in, and detract from, the final product which is derived from the process, e.g., paper formed from an aqueous suspension of pulp. Furthermore, when the contaminated water is involved in a heat exchange process, as either the "hot" or "cold" medium, scale will be formed upon the heat exchange surfaces which are contacted by the water. Such scale formation forms an insulating or thermal opacifying barrier which impairs heat transfer efficiency as well as impeding flow through the system.

While calcium sulfate and calcium carbonate are primary contributors to scale formation, other salts of alkaline-earth metals and the aluminum silicates are also offenders, e.g., magnesium carbonate, barium sulfate, the aluminum silicates provided by silts of the bentonitic, illitic, kaolinitic, etc., types.

Many other industrial waters, while not being scale forming, tend to be corrosive. Such waters, when in contact with a variety of metal surfaces such as ferrous metals, aluminum, copper and its alloys, tend to corrode one or more of such metals or alloys. A variety of compounds have been suggested to alleviate these problems. Such materials are low molecular weight polyacrylic acid polymers. Corrosive waters of this type are usually acidic in pH and are commonly found in closed recirculating systems.

Numerous compounds have been added to these industrial waters in an attempt to prevent or reduce scale and corrosion. One such class of materials are the well known organophosphonates which are illustrated by the compounds hydroxyethylidene diphosphonic acid (HEDP) and phosphonobutane tricarboxylic acid (PBTC). Another group of active scale and corrosion inhibitors are the monosodium phosphinicobis (succinic acids) which are described in U.S. Pat. No. 4,088,678.

Most industrial waters contain alkaline earth metal cations, such as calcium, barium, magnesium, etc. and several anions such as bicarbonate, carbonate, sulfate, oxalate, phosphate, silicate, fluoride, etc. When combinations of these anions and cations are present in concentrations which exceed the solubility of their reaction products, precipitates form until these product solubility concentrations are no longer exceeded. For example, when the concentrations of calcium ion and carbonate ion exceed the solubility of the calcium carbonate reaction products, a solid phase of calcium carbonate will form. Calcium carbonate is the most common form of scale.

Solubility product concentrations are exceeded for various reasons, such as partial evaporation of the water phase, change in pH, pressure or temperature, and the introduction of additional ions which form insoluble compounds with the ions already present in the solution.

As these reaction products precipitate on surfaces of the water carrying system, they form scale or deposits. This accumulation prevents effective heat transfer, interferes with fluid flow, facilitates corrosive processes and harbors bacteria. This scale is an expensive problem in many industrial water systems causing delays and shutdowns for cleaning and removal.

Scale deposits are generated and extended principally by means of crystal growth; and various approaches to reducing scale development have accordingly included inhibition of crystal growth, modification of crystal growth and dispersion of the scale-forming minerals.

Many organophosphorus compounds have been disclosed as scale inhibitors. For example, N,N-bis (phosphonomethyl)-2-amino-1-propanol and derivatives are disclosed in U.S. Pat. No. 5,259,974; N-substituted aminoalkane-1,1-diphosphonic acids are disclosed in U.S. Pat. No. 3,957,160; and propane 1,3 disphosphonic acids are disclosed in U.S. Pat. No. 4,246,103. A combination of a 1-hydroxypropylidene-1,1-diphosphonic acid and a water soluble polymer for controlling the deposition of scale-imparting precipitates is disclosed in U.S. Pat. No. 5,500,128. Further, N-bis(phosphonomethyl) amino acids for the prevention of calcium carbonate scale are disclosed in U.S. Pat. Nos. 5,414,112 and 5,478,476. 1,1 diphosphonic acid compounds are disclosed in U.S. Pat. Nos. 3,617,576, 4,892, 679 and 4,172,787. However, the ether 1,1-diphosphonates described herein are structurally different from the compounds cited above. One advantage of the ether 1,1-diphosphonates over conventional treatments is that they can be used in conjunction with other water treatment agents such as biocides, without causing significant degradation of those other treatment agents. Furthermore, the diphosphonates described herein are more efficient than conventional treatments.

SUMMARY OF THE INVENTION

The invention is a method for the prevention of scale formation on metal or other surfaces in contact with scale-forming industrial water with an effective scale-inhibiting amount of an ether 1,1-diphosphonate of the general formula:

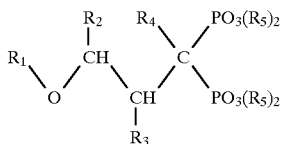

The invention is also a method for the prevention of corrosion on metal surfaces in contact with corrosive industrial water with an effective corrosion-inhibiting amount of an ether 1, 1-diphosphonate of the same general formula. A preferred ether 1,1-diphosphonate is 1,1, diphosphono-4,7-dioxaoctane for both methods.

DESCRIPTION OF THE INVENTION

The invention is a method for preventing scale formation on metal surfaces in contact with scale-forming industrial water which comprises treating said water with an effective scale-inhibiting amount of an ether 1,1-diphosphonate of formula (I)

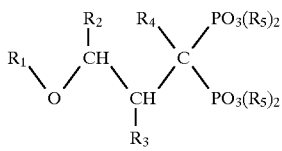

wherein $R_4$ is selected from the group consisting of hydrogen and $C_1$–$C_3$ alkyl groups; $R_2$ and $R_3$ are selected from the group consisting of hydrogen and methyl; $R_5$ is selected from the group consisting of hydrogen, metal cations and ammonium cations; and $R_1$ is selected from the group consisting of $C_1$–$C_{30}$ alkyl groups and $C_1$–$C_{30}$ ethers.

The industrial water may be cooling water, or industrial process water. A preferred ether 1,1-diphosphonate is 1,1-diphosphono-4,7-dioxaoctane. The scale may be calcium carbonate. The cooling water may contain a biocide. Moreover, the cooling water may contain other corrosion inhibitors, or other scale inhibitors.

The invention is also a method for preventing corrosion on metal surfaces in contact with corrosive industrial water which comprises treating said water with an effective corrosion-inhibiting amount of an ether 1,1-diphosphonate of formula (I)

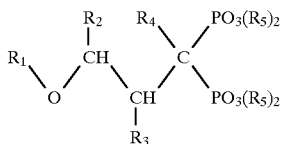

wherein $R_4$ is selected from the group consisting of hydrogen and $C_1$–$C_3$ alkyl groups; $R_2$ and $R_3$ are selected from the group consisting of hydrogen and methyl; $R_5$ is selected from the group consisting of hydrogen, sodium, metal cations and ammonium cations; and $R_1$ is selected from the group consisting of $C_1$–$C_{30}$ alkyl groups and $C_1$–$C_{30}$ ethers.

The industrial water may be cooling water, or industrial process water. A preferred ether 1, 1-diphosphonate is 1, 1-diphosphono-4, 7-dioxaoctane. The cooling water may contain a biocide. Moreover, the cooling water may contain other corrosion inhibitors, or other scale inhibitors.

The invention is also a method for preventing scale formation on metal surfaces in contact with scale-forming industrial water which comprises treating said water with an effective scale-inhibiting amount of an ether 1,1-diphosphonate of formula (I).

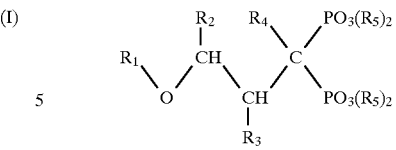

wherein $R_4$ is selected from the group consisting of hydroxy, amino and alkylamino; $R_2$ and $R_3$ are selected from the group consisting of hydrogen and methyl; $R_5$ is selected from the group consisting of hydrogen, sodium, metal cations and ammonium cations; and $R_3$ is selected from the group consisting of $C_1$–$C_{30}$ alkyl groups and $C_1$–$C_{30}$ ethers.

The industrial water may be cooling water, or industrial process water. The scale may be calcium carbonate. The cooling water may contain a biocide. Moreover, the cooling water may contain other corrosion inhibitors, or other scale inhibitors.

The invention is also a method for preventing corrosion on metal surfaces in contact with corrosive industrial water which comprises treating said water with an effective corrosion-inhibiting amount of an ether 1,1-diphosphonate of formula (I).

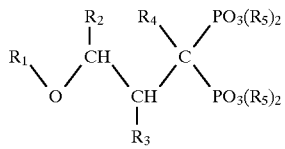

wherein $R_4$ is selected from the group consisting of hydroxy, amino and alkylamino; $R_2$ and $R_3$ are selected from the group consisting of hydrogen and methyl; $R_5$ is selected from the group consisting of hydrogen, sodium, metal cations and ammonium cations; and $R_1$ is selected from the group consisting of $C_1$–$C_{30}$ alkyl groups and $C_1$–$C_{30}$ ethers.

The industrial water may be cooling water. The cooling water may contain a biocide. Moreover, the cooling water may contain other corrosion inhibitors, or other scale inhibitors.

The invention is also an ether 1, 1 diphosphonate of the formula

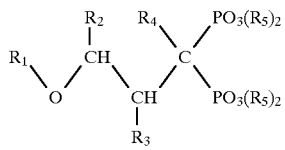

wherein $R_2$, $R_3$, $R_4$, and $R_5$ are hydrogen and $R_1$ is methyl.

Examples of compounds wherein $R_4$ is hydrogen or alkyl include 1,1-diphosphono-4-oxapentane, 2,2-diphosphono-5, 8-dioxanonane, and 2,2-diphosphono-5-oxahexane. Examples of compounds wherein $R_4$ is hydroxy, amino or alkylamino include 1,1-diphosphono-1-hydroxy-4,7-dioxaoctane, 1-amino-1, 1-diphosphono-4,7-dioxaoctane, 1,1-diphosphono-1-hydroxy-4-oxapentane and 1-amino-1, 1-diphosphono-4-oxapentane. As used herein, the term metal cations refers to cations of sodium, potassium, calcium and magnesium among others.

Typical metal surfaces in cooling water systems which may be subjected to corrosion or scale deposition are made of stainless steel, mild steel and copper alloys such as brass among others.

The method may be effective against other types of scale including magnesium silicate, calcium sulfate, barium sulfate, and calcium oxalate. The phosphonates are also effective in extremely hard water.

The method may be utilized in conjunction with other treatments, for example biocides. Stabilized bleach, chlorine, and hypobromite are applicable oxidizing biocides. Glutaraldehyde and mixtures of 5-chloro-2-methyl-4-isothiazolin-3-one and 2-methyl-4-isothiazolin-3-one are applicable non-oxidizing biocides. Additionally, the method may be utilized in conjunction with other corrosion and scale inhibitors. Thus, the phosphonates may be effective in combination with other inhibitors such as HEDP, PBTC, MDP, hexamethylenediamine-N,N,N'N'-tetra (methylenephosphonic acid), amino and tris (methylenephosphonic acid). The phosphonates may also be effectively utilized in conjunction with other polymeric treating agents, for example anionic polymers of under 200,000 MW. Such polymers include acrylic, methacrylic or maleic acid containing homo-, co- or ter-polymers.

The phosphonates may be added to the scale-forming or corrosive industrial process water in an amount from about 0.01 ppm to about 500 ppm. Preferably, the phosphonates may be added in an amount from about 0.01 ppm to 50 ppm. Most preferably, the phosphonates may be added in an amount of from about 1 ppm to about 25 ppm.

The following examples are presented to describe preferred embodiments and utilities of the invention and are not meant to limit the invention unless otherwise stated in the claims appended hereto.

EXAMPLE 1

The following is a procedure for the synthesis of 1,1-diphosphono-4,7-dioxaoctane (DPDO). Under an inert nitrogen atmosphere, sodium hydride (2.01 g, 0.088 mole) was combined with 200 mL dry tetrahydrofuran (THF) in a three-necked 500 mL roundbottom flask equipped with a nitrogen sweep and magnetic stirrer. The resulting suspension was cooled to $-10°$ C. in an ice/salt bath and stirred. A solution of tetraisopropyl methylenediphosphonate (27.5 g, 0.08 mole) dissolved in 30 mL dry THF was then added dropwise over a 90 minute period via an addition funnel. The reaction mixture was then allowed to stir for 30 min at $-10°$ C. and 1 hour at room temperature. A solution of 1-bromo-2-(2-methoxyethoxy)ethane (16.8 g, 0.092 mole) dissolved in 25 mL dry THF was then added dropwise over a 1 hour period. The reaction solution was then allowed to stir for 2 hours at room temperature and overnight (18 hours) at reflux. The reaction was then quenched with 5 mL 10 wt % ammonium chloride, filtered, concentrated, and dissolved in 500 mL ethyl acetate. The ethyl acetate solution was washed in a separatory funnel with saturated sodium chloride, dried with magnesium sulfate, filtered, and concentrated to 33.1 g amber oil product. The product was comprised of a mixture of the tetraisopropyl ester of 1, 1-diphosphono-4, 7-dioxaoctane/tetraisopropyl methylenediphosphonate/phosphorus-containing byproducts in a 56/35/9 mole ratio, along with some unreacted bromo-2-(2-methoxyethoxy) ethane.

The intermediate alkylation product mixture (32 g) described above was placed in a 2 L round bottom flask. A solution of 5% hydrochloric acid (836 g) containing cetyltrimethylammonium chloride (0.020 g) was then added slowly with stirring. The reaction was then heated to reflux and stirred for 24 hours. The reaction solution was then concentrated to 19.4 g oil, then dissolved in water to a total weight of 149 g. The product was analyzed for total phosphorus content and by phosphorus and carbon NMR, which showed a 9.2 wt % mixture of DPDO/(MDP) methylene diphosphonate/phosphorus-containing byproduct in a 54/38/8 mole ratio.

EXAMPLE 2

The intermediate alkylation product mixture described in Example 1, containing the isopropyl esters of DPDO and MDP, was purified by fractional distillation under reduced pressure. The purified tetraisopropyl ester of DPDO was collected at 145° C. head temperature/0.08 mm Hg. To 1.9 g of pure DPDO ester (92/0/8 DPDP ester/MDP ester/phosphorus-containing byproduct by phosphorus NMR) was added 5% hydrochloric acid (49.6 g) containing cetyltrimethylammonium chloride (0.010 g). The mixture was stirred and heated to reflux for 48 hours, concentrated to an oil, and dissolved in water to a total weight of 7.6 g. The product was analyzed for total phosphorus content and by phosphorus and carbon NMR, which showed a 13.8 wt % mixture of DPDO/MDP/phosphorus-containing byproduct in a 91/0/9 mole ratio.

EXAMPLE 3

A hardness solution of calcium and magnesium in a 2:1 Ca:Mg ratio in water was prepared, along with an alkaline solution of sodium carbonate/sodium bicarbonate buffered at pH 10. Both solutions were simultaneously added to 200 mL of an inhibitor test solution. The pH of the inhibitor test solution was adjusted to between 7 and 10. Calcium carbonate precipitation was detected by turbidity using a Brinkman PC-800 Colorimeter (420 nm wavelength) which was connected to a strip chart recorder. The hardness solution was prepared by adding 3.80 g calcium acetate and 2.57 g magnesium acetate tetrahydrate to distilled water (100 mL total volume). The alkaline solution was prepared by adding 2.01 g sodium bicarbonate and 1.27 g sodium carbonate to distilled water (100 mL total volume). A Masterflex pump delivered the hardness and alkaline solutions at 2.0 mL/min to the magnetically stirred test solution. All solutions were aqueous and maintained at a constant temperature of 45° C. The titration endpoint, expressed as the maximum calcium concentration (as calcium carbonate) before the onset of turbidity, was calculated from the elapsed time to a turbidity inflection on the strip chart recorder.

Higher endpoint values indicate a compound's increased ability to prevent scale precipitation. The test results, presented below in Table I, indicate that the inhibitors of the instant invention are superior to the currently used treatment agents PBTC and HEDP.

TABLE I

| | Endpoint (ppm Ca $CO_3$) | |
|---|---|---|
| Inhibitor | 10 ppm dose | 200 ppm dose |
| Example 1[1] | 410 | 660 |
| PBTC[2] | 390 | 430 |
| HEDP[3] | 350 | 190 |
| Example 2[4] | 410 | 680 |

[1]= 1,1-diphosphono-4,7-dioxaoctane, synthesized according to the procedure in Example 1
[2]= 2-phosphonobutane-1,2,4-tricarboxylic acid
[3]= 1-hydroxyethylidene-1,1-diphosphonic acid
[4]= 1,1-diphosphono-4,7-dioxaoctane, synthesized according to the procedure in Example 2

EXAMPLE 4

The constant composition technique was used to evaluate relative compound effectiveness regarding crystal growth inhibition. This method uses seed crystals which are introduced into a supersaturated solution of the seed components and measures growth rates as titrants are consumed during the crystallization process.

The procedure is outlined as follows. A supersaturated solution of calcium and carbonate (s=3.3) is made in a double-walled glass cell with recirculating water to maintain a constant temperature. The mixing is done slowly to insure metastabilty. The ionic strength is then adjusted with NaCl and the pH brought up to the desired value with dilute NaOH. Calcium carbonate seed crystals are then added. Characterization of the seed by scanning electron microscopy and triple point BET analysis indicated the particles were normal rhombohedrons c.a. 10 $\mu$m on a side and had a specific surface area of 0.38 $m^2$/gm.

As the experiment runs, calcium and carbonate/bicarbonate titrants are fed to maintain a pH of 8.5. The titrant concentrations are chosen so that the feed rate is not too fast or slow (typically 0.01M for 100 mg seed or 0.1M for 1 g seed) and are corrected for the subsequent dilution of each by the other. The consumption of titrants is measured as a function of time to obtain the growth rate. Inhibitor is typically added after 5 mls of both titrants have been fed so that the intrinsic growth rate can be observed prior to inhibitor addition.

Data is analyzed by multiplying the X values (time) by a normalization factor. This factor is obtained by dividing the slope observed just before inhibitor addition by an average slope determined from six replicate measurements. This operation compensates for different initial growth rates which are very dependent upon specific seed surface area and other environmental factors. The resulting data is a quantitative number (induction time) describing the relative ability of a particular compound to inhibit crystal growth.

To obtain the results of Table II, the above described procedure was used to determine the crystal growth inhibition of 500 mg of calcite seed in a total water volume of 305 mls. 0.2 ppm of each inhibitor to be tested was added to the calcite containing solution.

The results of Table II show that the 1,1-diphosphono-4,7-dioxaoctane inhibitor of the instant invention (Example 2) gives a surprisingly long inhibition time, and is among the most effec tive inhibitor s tested. The superior inhibition of the inhibitor described in Example 2 compared to a structurally similar compound, 3,6,9-trioxa-1-hydroxydecone-1,1-diphosphonic acid as disclosed in U.S. Pat. No. 4,892,679 was unanticipated and demonstrates the novel aspect of this invention.

TABLE II

Calcite Crystal Growth Inhibition Results

| Inhibitor | Inhibition Time (min) |
|---|---|
| 1-hydroxyethylidene-1,1-diphosphonic acid | 1000 |
| Example 2[1] | 900 |
| 2-phosphonobutane-1,2,4 tricarboxylic acid | 800 |
| amino tris methylene phosphonic acid | 550 |
| 3,6,9-trioxa-1-hydroxydecane-1,1-diphosphonic acid | 400 |

[1]= 1,1-diphosphono-4,7-dioxaoctane, synthesized according to the procedure in Example 2.

EXAMPLE 5

The stability of a potential inhibitor towards oxidation by biocides is an important factor with regard to performance in an actual cooling tower environment. In order to assess the relative stability of this new chemistry, its degradation to inorganic phosphate was measured in the presence of hyponchlorite.

A synthetic water was made consisting of 500 ppm calcium, 250 ppm magnesium, and 500 pm "M" alkalinity (bicarbonate), all as $CaCO_3$. The inhibitor was added at 25 ppm, as actives, prior to the bicarbonate to aid in preventing precipitation. Sodium hypochlorite, as a 5.25% bleach solution was then added so that a free residual of 40 ppm was measured in a blank solution using the Hach DPD method (N,N-diethyl-p-phenylenediamine indicator). The data in Table III shows the: percent depletion of hypochlorite after 24 hours which, assuming pure compounds, is a function of the stability of the molecule. The results show that DPDO is stable in the presence of oxidizing biocides, producing no hypochlorite depletion over a 24 hour period. Structurally similar ether phosphonates such as N,N-bis (phosphonomethyl)-2-amino-1-propanol methyl ether as disclosed in U.S. Pat. No. 5,259,974 are unstable and consume 100% of the hypochlorite as they decompose.

TABLE III

Chlorine Stability Results

| Inhibitor | % Depletion |
|---|---|
| Blank | 0 |
| Example 2 | 0 |
| 2-phosphonobutane-1,2,4-tricarboxylic acid | 5 |
| 1-hydroxyethylidene-1,1-diphosphonic acid | 21 |
| morpholinomethane-diphosphonic acid | 25 |
| N,N-bis(phosphonomethyl)-2-amino-1-propanol methyl ether | 100 |

EXAMPLE 6

The following dispersancy test procedure was utilized to obtain the results shown in Table IV. 200 mL of a test solution containing 20 ppm of a modified polyacrylate polymer dispersant and 20 ppm of phosphonate inhibitor(s) dissolved in distilled water was prepared. Then, the test solution was added to a 250 mL erlenmeyer flask magnetically stirred at 40° C. Hardness and m-alkalinity were added to the solution over seven minutes to achieve a final solution composition (ppm as $CaCO_3$) of 700 ppm $Ca^{2+}$, 350 ppm $Mg^{2+}$, and 700 ppm $CO_3{}^{2-}$. As calcium carbonate precipitation proceeds, a particle monitor responds to the fraction of calcium carbonate particles greater than 0.5 microns in diameter. The more effectively dispersed the calcium carbonate particles, the lower the fraction of large particle agglomerates. Better performing test solutions are indicated by (1) lower particle monitor intensities, and (2) intensity maxima achieved at times $\geq$60 minutes.

The results show that DPDO is the best performing phosphonate for enhancing calcium carbonate particle dispersancy because it generates (1) the smallest particle monitor intensity and (2) the signal maximum is reached at a time $\geq$60 minutes. Moreover, the addition of DPDO to the other phosphonates enhances the dispersancy performance of those test solutions by (1) reducing the particle monitor intensity and (2) postponing the signal maximum to times $\geq$60 minutes.

TABLE IV

| Phosphonate (20 ppm total actives)[1] | Particle Monitor Intensity | time |
|---|---|---|
| Blank | 100 | 10 minutes |
| methylene diphosphonate | 67 | 20 minutes |
| 1-hydroxyethylidene-1,1-diphosphonic acid | 68 | 20 minutes |
| 2-phosphonobutane- | 56 | 45 minutes |

TABLE IV-continued

| Phosphonate (20 ppm total actives)[1] | Particle Monitor Intensity | time |
|---|---|---|
| 1,2,4 tricarboxylic acid Example 2 | 9 | ≧60 minutes |
| Example 1 | 29 | ≧60 minutes |
| 1-hydroxyethylidene-1,1-diphosphonic acid + 1,1-diphosphono-4,7-dioxaoctane | 8 | ≧60 minutes |
| 2-phosphonobutane-1,2,4 tricarboxylic acid + 1-diphosphono-4,7-dioxaoctane | 0 | ≧60 minutes |

[1]Blank = 20 ppm polymer dispersant; phosphonate mixtures contain 60 mole % DPDO.

EXAMPLE 7

The following procedure was utilized to determine the calcium tolerance of phosphono group containing compounds. Two solutions were made up. The first contained 1000 mL of a 1000 ppm Ca solution (as $CaCO_3$) at a bath temperature of 45° C. was adjusted to pH 10.5 by dropwise addition of dilute NaOH. The second contained 1000 mL of a 1000 ppm inhibitor solution at a bath temperature of 45° C. was adjusted to pH 10.5 by dropwise addition of dilute NaOH. The second solution was added to the first solution which was magnetically stirred, at a rate of 1.0 mL/min with the solution transmittance recorded at a wavelength of 420 nm. The endpoint is reached when enough calcium phosphonate precipitation occurs to "cloud" the solution to 96% of the initial transmittance.

The results were summarized in Table V. It is evident that the DPDO prevents precipitation for a much longer time than other currently available treatments.

TABLE V

| Inhibitor | endpoint (minutes) |
|---|---|
| PBTC[1] | 6 |
| HEDP[2] | 8 |
| DPDO[3] | >55 |

[1]= 2-phosphonobutane-1,2,4-tricarboxylic acid
[2]= 1-hydroxyethylidene-1,1-diphosphonic acid
[3]= 1,1-diphosphono-4,7-dioxaoctane, synthesized according to the procedure in Example 2

Changes can be made in the composition, operation and arrangement of the method of the present invention described herein without departing from the concept and scope of the invention as defined in the following claims:

We claim:

1. A method for preventing scale formation on metal surfaces in contact with scale-forming industrial water which comprises treating said water with an effective scale-inhibiting amount of an ether 1,1-diphosphonate of formula (I)

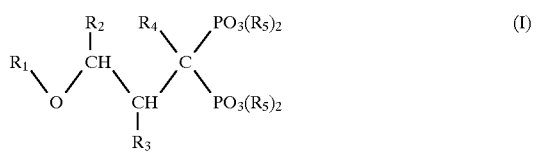

wherein $R_4$ is selected from the group consisting of hydrogen and $C_1$–$C_3$ alkyl groups; $R_2$ and $R_3$ are selected from the group consisting of hydrogen and methyl; $R_5$ is selected from the group consisting of hydrogen, metal cations and ammonium cations; and $R_1$ is selected from the group consisting of $C_1$–$C_{30}$ alkyl groups and $C_1$–$C_{30}$ ethers.

2. The method of claim 1 wherein the industrial water is cooling water.

3. The method of claim 1 wherein the ether 1,1-diphosphonate is 1,1-diphosphono-4,7-dioxaoctane.

4. The method of claim 1 wherein the scale is calcium carbonate.

5. The method of claim 2 wherein the cooling water contains a biocide.

6. The method of claim 2 wherein the cooling water contains corrosion inhibitors.

7. The method of claim 2 wherein the cooling water contains at least a second scale inhibitor.

8. The method of claim 1 wherein the industrial water is industrial process water.

9. A method for preventing corrosion on metal surfaces in contact with corrosive industrial water which comprises treating said water with an effective corrosion-inhibiting amount of an ether 1,1-diphosphonate of formula (I)

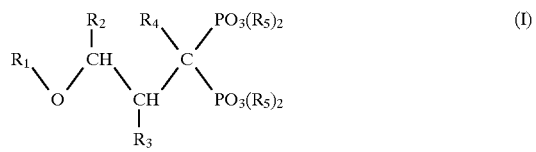

wherein $R_4$ is selected from the group consisting of hydrogen and $C_1$–$C_3$ alkyl groups; $R_2$ and $R_3$ are selected from the group consisting of hydrogen and methyl; $R_5$ is selected from the group consisting of hydrogen, sodium, metal cations and ammonium cations; and $R_1$ is selected from the group consisting of $C_1$–$C_{30}$ alkyl groups and $C_1$–$C_{30}$ ethers.

10. The method of claim 9 wherein the industrial water is cooling water.

11. The method of claim 9 wherein the ether 1,1-diphosphonate is 1,1-diphosphono-4,7-dioxaoctane.

12. The method of claim 9 wherein the cooling water contains a biocide.

13. The method of claim 10 wherein the cooling water contains at least a second corrosion inhibitor.

14. The method of claim 2 wherein the cooling water contains scale inhibitors.

15. The method of claim 9 wherein the industrial water is industrial process water.

16. A method for preventing scale formation on metal surfaces in contact with scale-forming industrial water which comprises treating said water with an effective scale-inhibiting amount of an ether 1,1-diphosphonate of formula (I).

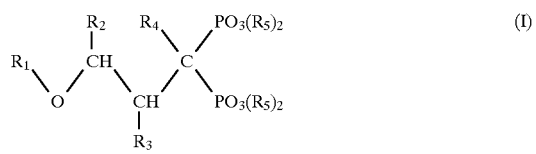

wherein $R_4$ is selected from the group consisting of hydroxy, amino and alkylamino; $R_2$ and $R_3$ are selected from the group consisting of hydrogen and methyl; $R_5$ is selected from the group consisting of hydrogen, sodium, metal cations and ammonium cations; and $R_1$ is selected from the group consisting of $C_1$–$C_{30}$ alkyl groups and $C_1$–$C_{30}$ ethers.

17. The method of claim 16 wherein the industrial water is cooling water.

18. The method of claim 16 wherein the scale is calcium carbonate.

19. The method of claim 17 wherein the cooling water contains a biocide.

20. The method of claim 17 wherein the cooling water contains corrosion inhibitors.

21. The method of claim 17 wherein the cooling water contains at least a second scale inhibitor.

22. The method of claim 16 wherein the industrial water is industrial process water.

23. A method for preventing corrosion on metal surfaces in contact with corrosive industrial water which comprises treating said water with an effective corrosion-inhibiting amount of an ether 1,1-diphosphonate of formula (I)

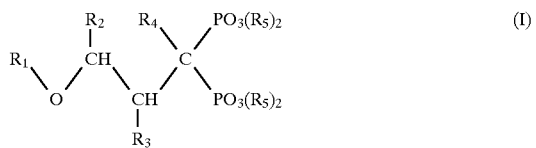

wherein $R_4$ is selected from the group consisting of hydroxy, amino and alkylamino; $R_2$ and $R_3$ are selected from the group consisting of hydrogen and methyl; $R_5$ is selected from the group consisting of hydrogen, sodium, metal cations and ammonium cations; and $R_1$ is selected from the group consisting of $C_1$–$C_{30}$ alkyl groups and $C_1$–$C_{30}$ ethers.

24. The method of claim 23 wherein the industrial water is cooling water.

25. The method of claim 23 wherein the cooling water contains further comprising a biocide.

26. The method of claim 2 wherein the cooling water contains at least a second corrosion inhibitor.

27. The method of claim 24 wherein the cooling water contains scale inhibitors.

28. The method of claim 23 wherein the industrial water is industrial process water.

* * * * *